(12) United States Patent
Zalevsky

(10) Patent No.: US 6,283,063 B1
(45) Date of Patent: Sep. 4, 2001

(54) REFREEZABLE AND RESUSABLE CHEWABLE PET TOY AND METHOD OF PREPARING AND USING THE SAME

(76) Inventor: Eric M. Zalevsky, 947 Cimarron Dr., Pittsburgh, PA (US) 15235

( * ) Notice: Subject to any disclaimer, the term of this patent is extended or adjusted under 35 U.S.C. 154(b) by 0 days.

(21) Appl. No.: 09/369,368

(22) Filed: Aug. 6, 1999

Related U.S. Application Data

(60) Provisional application No. 60/095,012, filed on Aug. 1, 1998.

(51) Int. Cl.$^7$ .................................................. A01K 29/00
(52) U.S. Cl. ........................................... 119/707; 119/709
(58) Field of Search ............................ 119/709, 710, 119/707; 604/291; 62/1

(56) References Cited

U.S. PATENT DOCUMENTS

| | | |
|---|---|---|
| 1,149,170 | 8/1915 | Allis . |
| 1,265,926 | 5/1918 | Ludlam . |
| 2,185,547 | 1/1940 | Fowler ........................................ 46/1 |
| 3,283,758 | 11/1966 | Killebrew ............................ 128/359 |
| 4,771,733 | 9/1988 | Axelrod ............................. 119/29.5 |
| 4,928,632 | 5/1990 | Gordon ............................. 119/29.5 |
| 5,263,436 | 11/1993 | Axelrod ............................. 119/710 |
| 5,447,532 | 9/1995 | Furuya ............................. 607/114 |
| 5,467,741 * | 11/1995 | O'Rourke ............................ 119/710 |
| 5,560,320 * | 10/1996 | Plunk ............................. 119/709 |
| 5,673,653 * | 10/1997 | Sherrill ............................. 119/709 |
| 5,682,838 * | 11/1997 | Reich ............................. 119/709 |
| 5,857,431 * | 1/1999 | Peterson ............................. 119/710 |
| 5,947,061 * | 9/1999 | Markham et al. ...................... 119/710 |

* cited by examiner

Primary Examiner—Charles T. Jordan
Assistant Examiner—Elizabeth Shaw
(74) Attorney, Agent, or Firm—Michael R. Swartz; John R. Flanagan

(57) ABSTRACT

A chewable pet toy has an outer sheath defining an interior cavity and made of a flexible liquid permeable material and an inner body made of a material capable of soaking up a liquid and being disposed within the interior cavity of the outer sheath. The inner body is captured within the outer sheath and the liquid may pass into and from the inner body through the outer sheath and the liquid soaked up by the inner body may become frozen and melt so that the outer sheath and the inner body will remain wet while and after the liquid melts and while the toy is being chewed on by a pet. The inner body further is made of a material capable of assuming a semi-rigid and semi-flexible condition when the liquid therein becomes frozen and a substantially flexible condition when the liquid therein is melted. The water soaked toy is stored in a resealable bag made of a liquid impermeable material during freezing of the toy. The toy is prepared and then used by soaking the toy in a liquid, placing and sealing the liquid soaked toy in the resealable bag, freezing the liquid soaked toy while in the bag, removing the frozen toy from the bag, and then giving the frozen toy to a pet to chew on until the frozen liquid in the toy has melted and the wetness of the toy has substantially diminished. The toy can be repeatedly resoaked and refrozen and given to the pet for continued reuse.

24 Claims, 2 Drawing Sheets

REFREEZABLE AND RESUSABLE CHEWABLE PET TOY AND METHOD OF PREPARING AND USING THE SAME

This patent application claims the benefit of U.S. provisional application No. 60/095,012, filed Aug. 1, 1998.

BACKGROUND OF THE INVENTION

1. Field of the Invention

The present invention generally relates to toys for pets and, more particularly, is concerned with a refreezable and reusable chewable pet toy and a method of preparing and using the same.

2. Description of the Prior Art

Pets, such as dogs, have been known to chew on, tear and play with a variety of articles, such as rags, wash cloths and various garments. Dogs particularly enjoy chewing on and tearing such articles when they are wet. The bulkier and wetter the articles, the more dogs appear to enjoy this activity. While wet rags, wash cloths and many garments can soak up water, they do not adequately retain wetness and are frequently shredded and destroyed by the activity. Also, dogs particularly seem to like to chew on ice and ice cubes.

Various devices have been developed over the years for use as chewable toys for pets. Representative examples are disclosed in U.S. Pat. No. 1,265,926 to Ludlam, U.S. Pat. No. 1,149,170 to Allis, U.S. Pat. No. 2,185,547 to Fowler, U.S. Pat. No. 4,771,733 to Axelrod, U.S. Pat. No. 4,928,632 to Gordon, U.S. Pat. No. 5,263,436 to Axelrod, U.S. Pat. No. 5,682,838 to Reich, U.S. Pat. No. 5,857,431 to Peterson. While these prior art chewable pet toys may be satisfactory in use for the specific purposes for which they were designed, none would seem to provide an article which adequately retains wetness and is indestructible while being chewed on by a dog.

Consequently, a need still exists for a device which provides a solution to the aforementioned problem in the prior art without introducing any new problems in place thereof.

SUMMARY OF THE INVENTION

The present invention provides a refreezable and reusable chewable pet toy designed to satisfy the aforementioned need. The chewable pet toy can soak up water and be frozen in being prepared for use and then can gradually melt but retain its wetness over an extended period as the pet chews on it during use. In a repeatable manner, the toy is resoaked and refrozen and then reused. The toy includes an outer sheath of liquid permeable, but relatively tear resistant, material and an inner sponge capable of soaking up a liquid such as water being disposed within the outer sheath. Water may pass into and from the inner sponge through the outer sheath and while in the inner sponge may freeze and melt. The outer sheath and inner sponge of the toy remain wet during and after melting and while the toy is being chewed on by a dog. The toy may be repeatedly soaked and refrozen for continued reuse.

Accordingly, the present invention is directed to a chewable pet toy which comprises: (a) an outer sheath defining an interior cavity and made of a flexible liquid permeable material; and (b) an inner body made of a material capable of soaking up a liquid and being disposed within the interior cavity of the outer sheath such that the inner body is captured within the outer sheath and the liquid may pass into and from the inner body through the outer sheath and such that the liquid soaked up by the inner body may become frozen and melt so that the outer sheath and the inner body will remain wet while and after the liquid melts and while the toy is being chewed on by a pet.

More particularly, the tear resistant material of the outer sheath is a fabric comprised substantially of cotton, canvas or a plastic. Also, the outer sheath has an outer surface and a plurality of dimples spaced apart from one another and extending outwardly from the outer surface and being open to the interior cavity of the outer sheath. The outer sheath also has a plurality of holes each defined through one of the dimples thereof allowing for passage of the liquid therethrough. The inner body is a material capable of assuming a semi-rigid and semi-flexible condition when the liquid therein becomes frozen and a substantially flexible condition when the liquid therein is melted. Each of the outer sheath and the inner body has a substantially bow-tie shape resembling a dog bone. The inner body may repeatedly be resoaked with the liquid and then refrozen for continued reuse.

The present invention is also directed to a pet toy package comprising the above-described chewable pet toy in combination with a resealable bag made of liquid impermeable material.

The present invention is further directed to a method of preparing and using the chewable pet toy. The method comprises the steps of: (a) providing the above-described chewable pet toy; (b) soaking the toy with a liquid; (c) freezing the liquid soaked toy; and (d) giving the frozen toy to a pet to chew on until the frozen liquid in the toy has melted and the wetness of the toy has substantially diminished. The soaking step includes placing the toy in a liquid such that the toy soaks up and retains the liquid. The method further comprises, after the soaking step and before the freezing step, placing the toy soaked with the liquid in a resealable bag of a liquid impermeable material and sealing the bag such that no liquid may pass out of the bag. The freezing step includes freezing the liquid soaked toy while in the bag such that the toy is in a semi-rigid and semi-flexible condition when frozen. The method further comprises after the freezing step and before the giving step, removing the frozen toy from the bag. The method still further comprises the steps of repeatedly soaking and freezing the toy and giving the frozen toy to the pet for continued reuse.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 3 is transverse sectional view of the toy also taken along line 2—2 of FIG. 1 but showing the outer sheath and inner body together having a substantially compacted oblong transverse configuration when liquid in the inner body is melted and chewed on.

DETAILED DESCRIPTION OF THE INVENTION

Figure 1:
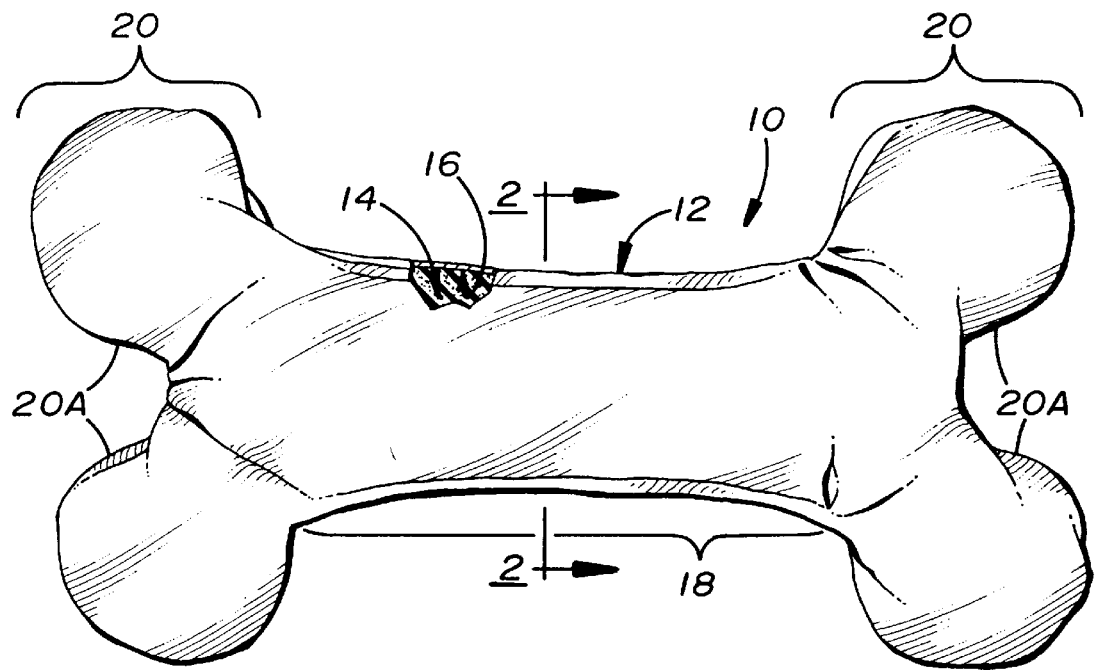
FIG. 1 is a top plan view of a chewable pet toy of the present invention.

In the following description, like reference characters designate like or corresponding parts throughout the several views. Also, in the following description, it is understood that terms such as "forward", "rearward", "left", "right", "upwardly", "downwardly", and the like, are words of convenience and are not construed to be limiting terms.

Figure 2:
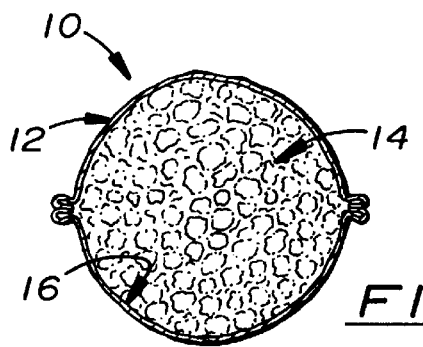
FIG. 2 is a transverse sectional view of the chewable pet toy taken along line 2—2 of FIG. 1 showing a flexible liquid permeable outer sheath and a liquid soaking inner body disposed within an interior cavity of the outer sheath and showing the outer sheath and inner body together having a substantially circular transverse configuration when liquid in the inner body is frozen.
Figure 3:
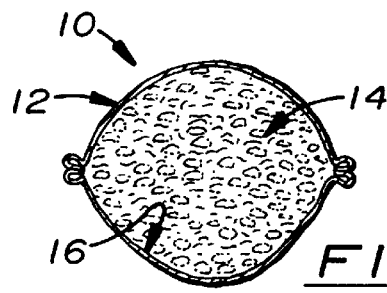

Referring to the drawings and particularly to FIGS. 1 to 3, there is illustrated a refreezable and reusable chewable pet toy, generally designated 10, of the present invention. Basically, the chewable pet toy 10 includes an outer cover or sheath 12 made of a flexible tear resistant liquid permeable material and an inner body 14 made of a material capable of soaking up liquid. The outer sheath 12 defines an interior cavity 16. The inner body 14 is disposed within the interior cavity 16 of the outer sheath 12 such that the inner body 14 is captured and wholly contained within the outer sheath 12. A liquid, such as water, (not shown) may pass into and from the inner body 14 through the outer sheath 12 so that the liquid in the inner body 14 may become frozen and may melt and the toy 10 will remain wet while and after the liquid melts and while the toy 10 is being chewed on by a pet, such as a dog (not shown). The material of the inner body 14 is also capable of assuming a semi-flexible and semi-rigid condition when the liquid therein becomes frozen and of assuming a substantially flexible condition when the liquid therein is melted. The outer sheath 12 and the inner body 14 preferably, although not necessarily, together provide the toy 10 with a shape resembling a dog bone. The toy 10 can be repeatedly resoaked with the liquid and then refrozen for continued reuse.

Referring now to FIGS. 1 to 3, 5 and 6, the outer sheath 12 may have several different embodiments. In a first exemplary embodiment, as shown in FIGS. 1 to 3, the outer sheath 12 is comprised of a substantially rugged fabric material, such as dense cotton or canvas, which does not tear easily, and thus is characterized as being tear resistant, when a dog bites and chews on the toy 10. The rugged fabric material is also of a type which is permeable to liquids, permitting the liquid, such as water, to pass through it. In an alternative embodiment, shown in FIGS. 5 and 6, the outer sheath 12 is comprised of a substantially a rubber or plastic material.

In both embodiments, the outer cover or sheath 12 has a substantially bow-tie shape which resembles a dog bone. The outer sheath 12 has a middle portion 18 and opposite end portions 20. The middle portion 18 is elongated and each end portion 20 is a pair of lobes 20A. The middle portion 18 has a size which is greater than a size of each end portion 20.

When comprised of rubber or plastic material, the outer sheath 12 defines a plurality of bubbles or dimples 22. The dimples 22 are spaced apart from one another and extend outwardly from an outer surface 24 of the outer sheath 12 and are open to the interior cavity 16. The dimples 22 preferably, although not necessarily, are arranged in a regular pattern on the middle and end portions 18 of the outer sheath 12, such as in laterally spaced rows extending along opposite sides of the middle and end portions 18, 20. The outer sheath 12 also has a plurality of holes 26. Each hole 26 is centrally defined through one of the dimples 22 of the outer sheath 12 allowing passage of the liquid therethrough.

The inner body 14 is substantially the same for both embodiments of the outer sheath 12. By way of example, the liquid soaking material of the inner body 14 can be a natural sponge or other synthetic materials with similar properties. The material of the inner body 14, such as a sponge, and preferably a natural sponge, takes on a semi-rigid and semi-flexible condition when the liquid therein is frozen. A characteristic of a sponge which is desirable for the toy 10 is that the sponge does not become entirely rigid but rather remains somewhat pliable when frozen such that the teeth of a dog will not penetrate through the outer sheath 12 and into the sponge of the inner body 14 when the dog chews on the toy 10. Consequently, the outer sheath 12 of the toy 10 is unlikely to be ripped open and destroyed by prolonged chewing by the dog. The sponge of the inner body 14 also maintains a substantially flexible condition when the liquid therein is melted. The outer sheath 12 and inner body 14 both warm up and thereby the liquid melts as the dog bites and chews on the toy 10. A portion of the liquid in the inner body 14 is squeezed out thereof during the biting and chewing on the toy 10 by the dog. With the portion of the liquid removed, the outer sheath 12 and inner body 14 may be squashed into a more compacted state, as seen in FIG. 3.

Figure 6:
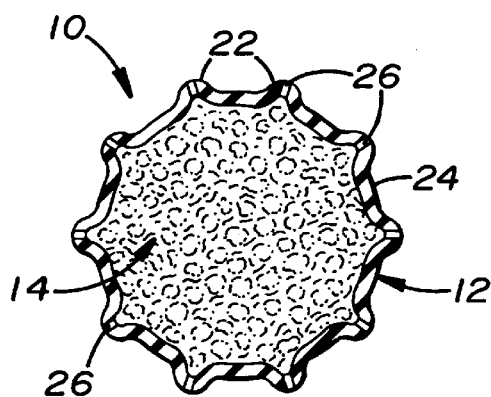
FIG. 6 is a transverse sectional view of the toy taken along line 6—6 of FIG. 5 similar to that of FIG. 2 showing the alternative embodiment of the toy.

The inner body 14, like the outer sheath 12, preferably, although not necessarily, has a substantially bow-tie shape which resembles a dog bone and which conforms to the shape of the outer sheath 12. The outer sheath 12 has a size which is slightly greater than that of the inner body 14 such that the inner body 14 fits snugly within the interior cavity 16 of the outer sheath 12. The filling of the toy 10 with water and the freezing of water in the soaked toy 10 will fill the cells 14A of the sponge or like material of the inner body 14 so as to cause the inner body 14 to expand or extend somewhat from the compacted state shown in FIG. 2 back to the natural state shown in FIG. 3. The outer sheath 12 and inner body 14 together have a substantially extended circular transverse configuration when the toy is soaked with liquid and the liquid is frozen in the toy 10, as shown in FIGS. 2 and 6. Melting of the liquid and chewing of the dog causes the inner body 14 of the toy 10 to compact to a substantially oblong transverse configuration, as shown in FIG. 3. The material of the inner body 14 is such that it may repeatedly be resoaked and refrozen for continued reuse.

Figure 4:
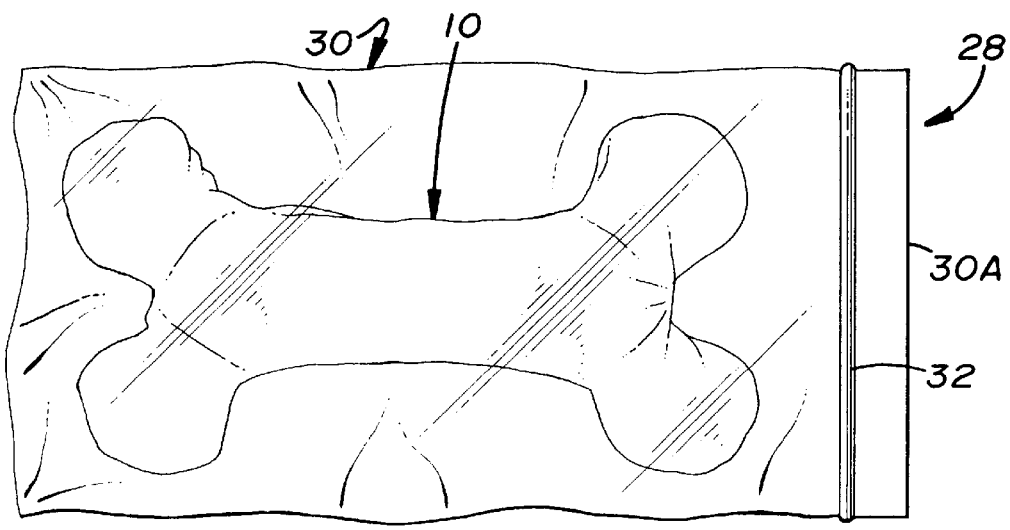
FIG. 4 is a top plan view of the toy of FIG. 1 shown on a reduced scale and disposed in a resealable bag for freezing the toy.
Figure 5:
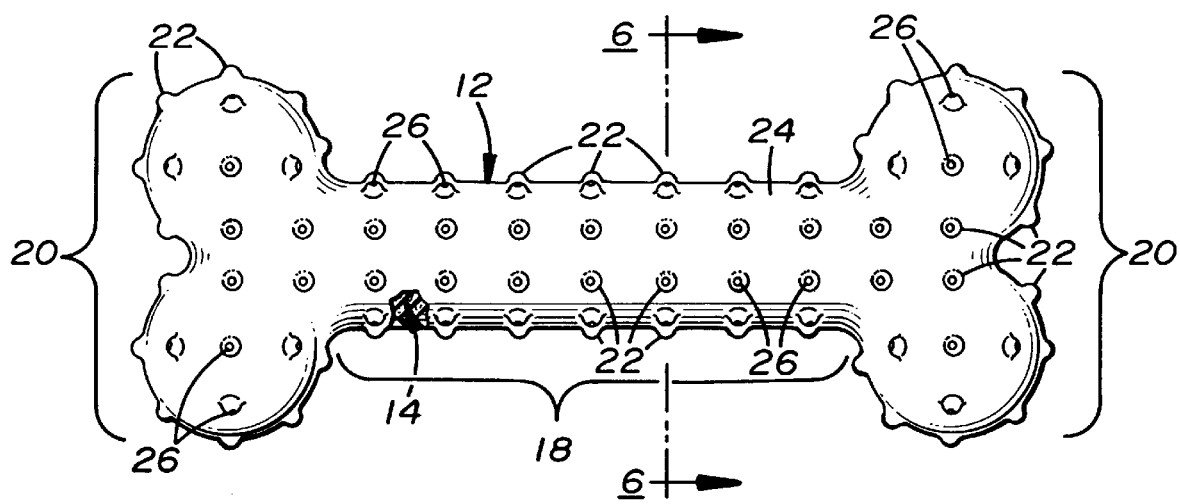
FIG. 5 is a top plan view of the toy showing an alternative embodiment of the outer sheath thereof having a plurality of dimples spaced apart from one another on and extending outwardly from an outer surface of the toy and being open to an interior cavity thereof and defining a plurality of holes each through one of the dimples thereof allowing for passage of liquid therethrough.

Referring to FIG. 4, there is depicted a pet toy package, generally, designated 28, comprising the above-described chewable pet toy 10 combination with a resealable bag 30 made of a flexible liquid impermeable material, such as a suitable plastic. The material of the bag 30 preferably is transparent. The bag 30 has an open end 30A with a reclosure feature thereon in the form of a slidable type lock 32 allowing opening and resealing of the bag 30. Since the wet toy 10 would leak liquid otherwise, the bag 30 confines an leaked liquid and has a sanitary function by separating the toy 10 from human food in a freezer.

The method of preparing and using the chewable pet toy 10 of the present invention involves the steps of providing the above-described chewable pet toy 10 and placing the toy 10 in a liquid, for instance in a pan filled with water, such that the toy 10 will soak up and retain the liquid. Once soaked with water, the toy 10 is then placed in the above-described resealable bag 30 and the bag 30 is sealed using the lock 32 such that no liquid may pass out of the bag 30. The bag 30 with the water-soaked toy 10 therein are then subjected to a source of freezing temperatures, such as the freezer compartment of a typical refrigerator (not shown), where the water soaked toy 10 becomes frozen while in the bag 30. In the frozen state, the toy 10 is in a semi-rigid and semi-flexible condition.

When it is desired to use the frozen toy 10, the bag 30 with the toy 10 therein are removed from the freezer compartment and the frozen toy is removed from the bag 30. The bag 30 may be retained for reuse or discarded and a new bag 30 can be used when it comes time to refreeze the toy 10. The frozen toy 10 is then given to the pet to chew on until the frozen liquid in the toy 10 has melted and the wetness of the toy 10 has substantially diminished. The method further comprises the steps of repeatedly resoaking and refreezing the toy 10 and giving the toy 10 to the pet for continued reuse.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. A chewable pet toy, comprising:
   (a) an outer sheath defining an inner cavity and made of a flexible liquid permeable material so as to allow a liquid to pass therethrough in either direction; and
   (b) an inner body of a material capable of soaking up a liquid and being disposed within said interior cavity of said outer sheath such that said inner body is captured within said outer sheath to determine and maintain the shape of the outer sheath, said flexible liquid permeable material of said outer sheath permitting the liquid to pass into and from said inner body through said outer sheath such that the liquid soaked up by said inner body may become frozen and melt so that said outer sheath and said inner body will remain wet while and after the liquid melts and while said toy is being chewed on by a pet.

2. The toy as recited in claim 1, wherein said inner body is a natural sponge.

3. The toy as recited in claim 1, wherein said tear resistant material of said outer sheath is a fabric comprised substantially of cotton.

4. The toy as recited in claim 1, wherein said tear resistant material of said outer sheath is a fabric comprised substantially of canvas.

5. The toy as recited in claim 1, wherein said tear resistant material of said outer sheath is a fabric comprised substantially of rubber.

6. The toy as recited in claim 1, wherein said outer sheath has an outer surface and a plurality of dimples spaced apart from one another and extending outwardly from said outer surface and being open to said interior cavity of said outer sheath.

7. The toy as recited in claim 6, wherein said outer sheath has plurality of holes each defined through one of said dimples thereof allowing for passage of the liquid therethrough.

8. The toy as recited in claim 1, wherein said inner body is made of a material capable of assuming a semi-rigid and semi-flexible condition when the liquid therein becomes frozen and a substantially flexible condition when the liquid therein is melted.

9. The toy as recited in claim 1, wherein each of said outer sheath and said inner body has a substantially bow-tie shape resembling a dog bone.

10. The toy as recited in claim 1, wherein said inner body is made of a material capable of being repeatedly resoaked with the liquid and then refrozen for continued reuse.

11. A pet toy package, comprising:
    (a) a chewable pet toy including
       (i) an outer sheath defining an inner cavity and made of a flexible liquid permeable material, and
       (ii) an inner body made of a material capable of soaking up a liquid and being disposed within said interior cavity of said outer sheath such that said inner body is captured within said outer sheath and the liquid may pass into and from said inner body through said outer sheath and such that the liquid soaked up by said inner body may become frozen and melt so that said outer sheath and said inner body will remain wet while and after the liquid melts and while said toy is being chewed on by a pet; and
    (c) a resealable bag made of a liquid impermeable material for enclosing said toy during freezing thereof and during periods of non-use of said toy.

12. The package as recited in claim 11, wherein said inner body of said toy is a natural sponge.

13. The package as recited in claim 11, wherein said outer sheath of said toy has an outer surface and a plurality of dimples spaced apart from one another and extending outwardly from said outer surface and being open to said interior cavity of said outer sheath.

14. The package as recited in claim 13, wherein said outer sheath of said toy has a plurality of holes each defined through one of said dimples thereof allowing for passage of the liquid therethrough.

15. A method of preparing and using a chewable pet toy, comprising the steps of:
    (a) providing a chewable pet toy having an outer sheath defining an interior cavity and made of a flexible liquid permeable material and an inner body made of a material capable of soaking up a liquid and being disposed within said interior cavity of said outer sheath such that said inner body is captured within said outer sheath and the liquid may pass into and from said inner body through said outer sheath;
    (b) soaking the toy with a liquid;
    (c) freezing the liquid soaked toy; and
    (d) giving the frozen toy to a pet to chew on until the frozen liquid in the toy has melted and the wetness of the toy has substantially diminished.

16. The method as recited in claim 15, wherein said providing step includes providing the inner body made of a material capable of assuming a semi-rigid and semi-flexible condition when the liquid therein becomes frozen and a substantially flexible condition when the liquid therein is melted.

17. The method as recited in claim 15, wherein said providing step includes providing the toy in a substantially bow-tie shape resembling a dog bone.

18. The method as recited in claim 15, wherein said soaking step includes placing the toy in a liquid such that the toy soaks up and retains the liquid.

19. The method as recited in claim 15, further comprising:

after said soaking step and before said freezing step, placing the toy soaked with the liquid in a resealable bag of a liquid impermeable material and sealing the bag such that no liquid may pass out of the bag.

20. The method as recited in claim 19, wherein said freezing step includes freezing the liquid soaked toy while in the bag.

21. The method as recited in claim 20, further comprising:

after said freezing step and before said giving step, removing the frozen toy from the bag.

22. The method as recited in claim 15, wherein said freezing step includes freezing the toy into a semi-rigid and semi-flexible condition.

23. The method as recited in claim 15, further comprising the steps of:

repeatedly soaking and freezing the toy and giving the frozen toy to the pet for continued reuse.

24. A method of preparing and using a chewable pet toy, comprising the steps of:

(a) providing a chewable pet toy having an outer sheath defining an interior cavity and made of a flexible liquid permeable material and an inner body made of a material capable of soaking up a liquid and being disposed within said interior cavity of said outer sheath such that said inner body is captured within said outer sheath and the liquid may pass into and from said inner body through said outer sheath;

(b) soaking the toy with a liquid by placing the toy in a liquid such that the toy soaks up and retains the liquid;

(c) placing the toy soaked with the liquid in a resealable bag of a liquid impermeable material and sealing the bag such that no liquid may pass out of the bag;

(d) freezing the toy while in the bag such that the toy is in a semi-rigid and semi-flexible condition when frozen;

(e) removing the frozen toy from the bag;

(f) giving the frozen toy to a pet to chew on until the frozen liquid in the toy has melted and the wetness of the toy has substantially diminished; and (g) repeatedly soaking and freezing the toy and giving the frozen toy to a pet for continued reuse.

* * * * *